(12) United States Patent
Meireles et al.

(10) Patent No.: US 12,362,068 B2
(45) Date of Patent: Jul. 15, 2025

(54) INTERPRETATION OF INTRAOPERATIVE SENSOR DATA USING CONCEPT GRAPH NEURAL NETWORKS

(71) Applicants: THE GENERAL HOSPITAL CORPORATION, Boston, MA (US); MASSACHUSETTS INSTITUTE OF TECHNOLOGY, Cambridge, MA (US)

(72) Inventors: Ozanan R. Meireles, Cambridge, MA (US); Yutong Ban, Boston, MA (US); Daniel A. Hashimoto, Boston, MA (US); Guy Rosman, Boston, MA (US); Thomas Ward, Boston, MA (US); Daniela Rus, Cambridge, MA (US)

(73) Assignees: THE GENERAL HOSPITAL CORPORATION, Boston, MA (US); MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 113 days.

(21) Appl. No.: 18/550,367

(22) PCT Filed: Mar. 28, 2022

(86) PCT No.: PCT/US2022/022218
§ 371 (c)(1),
(2) Date: Sep. 13, 2023

(87) PCT Pub. No.: WO2022/204605
PCT Pub. Date: Sep. 29, 2022

(65) Prior Publication Data
US 2024/0112809 A1    Apr. 4, 2024

Related U.S. Application Data

(60) Provisional application No. 63/166,816, filed on Mar. 26, 2021.

(51) Int. Cl.
*G16H 50/20* (2018.01)
*G16H 30/40* (2018.01)
*G16H 40/63* (2018.01)

(52) U.S. Cl.
CPC ............. *G16H 50/20* (2018.01); *G16H 30/40* (2018.01); *G16H 40/63* (2018.01)

(58) Field of Classification Search
CPC .......... A61B 90/361; A61B 2034/2065; G16H 40/20
See application file for complete search history.

(56) References Cited

U.S. PATENT DOCUMENTS

2020/0237452 A1* 7/2020 Wolf ..................... G06F 3/048

* cited by examiner

*Primary Examiner* — Joseph D Burgess
(74) *Attorney, Agent, or Firm* — Tarolli, Sundheim, Covell & Tummino LLP

(57) ABSTRACT

Systems and methods are provided for generating a statistical parameter representing a state of a surgical procedure from sensor data. Sensor data representing a time period. is received from a sensor. Numerical features representing the time period are generated from the sensor data. Each of a plurality of long short term memory units are updated according to the plurality of numerical features via a message passing process. The long short term memory units are connected to form a graph, with a first set of the long short term memory units representing a plurality of nodes of the graph and a second set of the long short term memory units representing a plurality of hyperedges of the graph. A statistical parameter representing a state of the surgical procedure for the time period is derived from an output of one of the long short term memory units and provided to a user.

19 Claims, 3 Drawing Sheets ial,2,068 B2

INTERPRETATION OF INTRAOPERATIVE SENSOR DATA USING CONCEPT GRAPH NEURAL NETWORKS

RELATED APPLICATIONS

The present application claims priority to U.S. Provisional Patent Application Ser. No. 63/166,816 filed Mar. 26, 2021 and entitled CONCEPT GRAPH NEURAL NETWORKS FOR SURGERY. The entire content of this application is incorporated herein by reference in its entirety for all purposes.

TECHNICAL FIELD

This disclosure relates to systems and methods for decision support and, in particular, is directed to systems and methods for interpretation of intraoperative sensor data using concept graph neural networks.

BACKGROUND

As surgical care quality increases with new technologies and greater understanding of surgical disease, gaps remain in both access to and quality of care for many patients. This has led to minimal volume pledges that restrict surgical procedures to surgeons and hospitals with an arbitrarily determined number of sufficient annual cases. Volume pledges have raised concerns over the potential regionalization of surgical care and the impact that regionalization may have on access to surgery, particularly for rural areas. High volume hospitals for complex operations are not readily accessible to many patients, and recent work has shown, for example, that rural patients with cancer are more likely to have their resections performed at a low-volume, yet local, hospital. There is also evidence to suggest that regionalization of care would disproportionately affect minorities and patients without private insurance, as they are most likely to have their operations performed at low-volume hospitals. Thus, the proposed redistribution of care with volume pledges may not be the best solution for all patients.

An estimated 234.2 million operations are performed annually worldwide, but surgeons learn from one patient at a time, limiting their knowledge on rate procedures. Residency is designed to give surgeons the fundamental skills necessary to apply and expand principles of safe surgery to each situation encountered in practice, even novel situations. However, residency relies on apprenticeship-like exposure to experienced surgeons. These experienced surgeons, with a wealth of experiential data, have limited availability. Training for rare cases has thus necessarily been left to a limited number of surgeons who complete sub-specialty fellowships which are often housed in high volume, urban academic centers, again leaving rural and minority populations with a disadvantage in access to care.

Previous attempts have been made to accumulate and distribute intraoperative decision-making models to surgeons to optimize surgical care. Cognitive task analysis (CTA) has been used to codify and distill experienced surgeons' knowledge into standardized checklists to assist in decision-making. In surgical patients, up to 67% of errors occur intraoperatively, and of those errors, 86% of errors are secondary to cognitive factors such as failures in judgment or memory that lead to poor decisions. However, CTA is limited by the fact that 50-75% of decisions made in surgery can be lacking in the conscious recall of surgeons due to either inexperience or automaticity, and these efforts have been time consuming and have not addressed morbidity and mortality at a large scale.

SUMMARY

In accordance with an aspect of the present invention, a system is provided. The system includes a sensor positioned to monitor a surgical procedure on a patient, a processor, and a non-transitory computer readable medium stores machine executable instructions for providing a statistical parameter representing a state of the surgical procedure for the time period. The machine executable instructions are executed by the processor to provide a sensor interface that receives sensor data from the sensor. The sensor data represents a time period of a plurality of time periods comprising the surgical procedure. A feature extractor generates a plurality of numerical features representing the time period from the sensor data.

A plurality of temporal processing network modules are each configured to receive the extracted plurality of numerical features. The plurality of temporal processing network modules are connected to form a graph, with a first set of the plurality of temporal processing network modules representing a plurality of nodes of the graph and a second set of the plurality of temporal processing network modules representing a plurality of hyperedges of the graph. Each of the plurality of temporal processing network modules are updated via a message passing process according to the location of the temporal processing network module within the graph. An output device provides a statistical parameter representing a state of the surgical procedure for the time period to a user. The statistical parameter representing the state of the surgical procedure for the time period is derived from an output of one of the plurality of temporal processing network modules In accordance with another aspect of the present invention, a method is provided. Sensor data representing a time period of a plurality of time periods comprising a surgical procedure on a patient. is received from a sensor positioned to monitor the surgical procedure. A plurality of numerical features representing the time period are generated from the sensor data. Each of a plurality of temporal processing network modules are updated according to the plurality of numerical features. The plurality of temporal processing network modules are connected to form a graph, with a first set of the plurality of temporal processing network modules representing a plurality of nodes of the graph and a second set of the plurality of temporal processing network modules representing a plurality of hyperedges of the graph. Each of the plurality of temporal processing network modules are updated via a message passing process according to the location of the temporal processing network module within the graph. A statistical parameter representing a state of the surgical procedure for the time period is provided to a user at an output device. The statistical parameter is derived from an output of one of the plurality of temporal processing network modules.

In accordance with yet another aspect of the present invention, a method is provided. A frame of video is received from a sensor positioned to monitor a surgical procedure on a patient. The frame of video represents a time period of a plurality of time periods comprising the surgical procedure. A plurality of numerical features representing the frame of video are generated at a convolutional neural network. Each of a plurality of long short term memory units are updated according to the plurality of numerical features. The plurality of long short term memory units are connected to form a graph, with a first set of the plurality of long short term memory units representing a plurality of nodes of the graph and a second set of the plurality of long short term memory units representing a plurality of hyperedges of the graph. The state of each of the first set of long short term memory units represents a concept associated with the surgery. Each of the plurality of long short term memory units are updated via a message passing process according to the location of the long short term memory unit within the graph. A statistical parameter representing a state of the surgical procedure for the time period is provided to a surgical assisted decision making system via a network interface. The statistical parameter representing the state of the surgical procedure for the time period is derived from an output of one of the plurality of long short term memory units.

DETAILED DESCRIPTION

Figure 1:
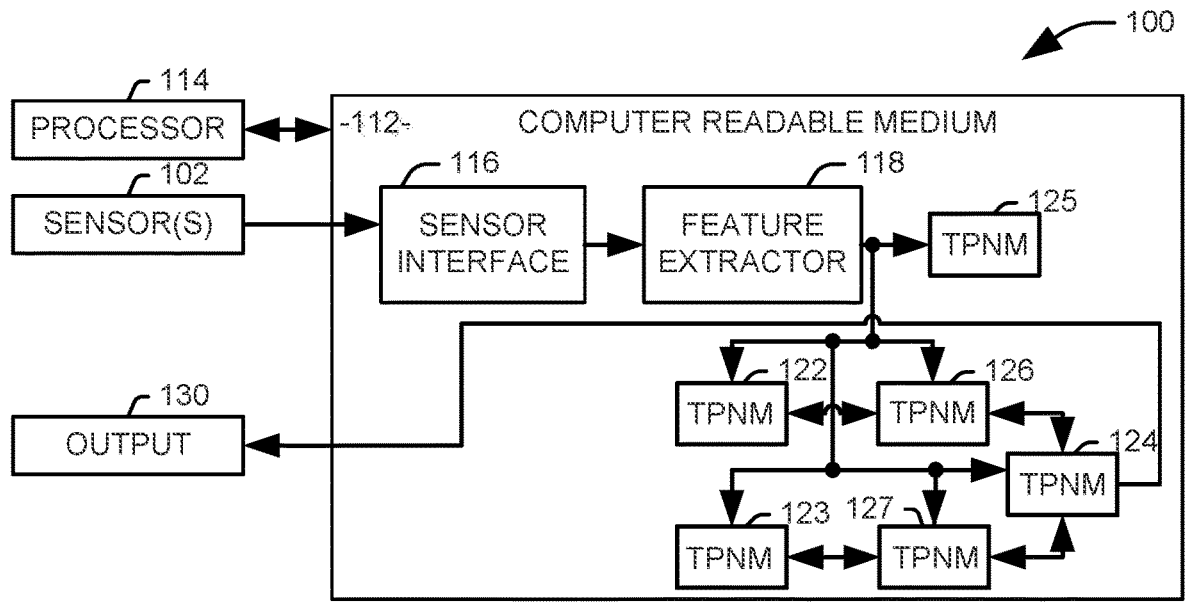
FIG. 1 illustrates an example of system for generating a statistical parameter representing a state of a surgical procedure from sensor data.

In many temporal analysis and prediction tasks, people leverage their conceptual understanding to make informed estimates. Specifically, when reasoning about surgical workflow, surgeons leverage previously internalized concepts and understandings of the procedure and anatomy to support their decision making, foresee future operative steps, and comprehend the overall progress of the procedure. The systems and methods presented herein focus on modeling different elements in surgery as concepts and analyze the relations among these concepts. Examples for such underlying concepts include surgical safety notions, such as the critical view of safety, and clinical variables, like the Parkland Grading Scale for Gallbladder Inflammation.

Correctly modelling the temporal evolution of different concepts and the relations of their underlying components is critical to the analysis of the surgery. Computational analyses of surgical video data, however, often do not account for the concepts explicitly, but rather focus on a specific task at hand, such as phase recognition or tool segmentation. While achieving good results for specific procedures and machine learning (ML) tasks, such approaches do not easily generalize across ML tasks and do not lend themselves to interpretation. This limits the clinical value as it fails to account for all interacting components of surgery, which is especially important in comprehension of surgical workflow as a whole. In addition, surgical decision making is influenced by a large set of diverse concepts, unlike many other fields to which machine learning is applied, such as image classification or speech processing. Correctly modelling these concepts will offer a strong structural prior for data-driven models and a foundation for machine comprehension of the surgical workflow. The claimed systems and methods leverage these concepts to enhance computational support in surgical decision making, contributing to risk mitigation and reduction of morbidity and mortality of minimally invasive surgery.

The systems and methods presented herein seek to boost the effective experience of surgeons by data mining operative sensor data, such as video, to generate a collective surgical experience that can be utilized to provide automated predictive-assistive tools for surgery. Rapid advancements in streaming data analysis have opened the door to efficiently gather, analyze, and distribute collective surgical knowledge. However, simply collecting massive amounts of data is insufficient, and human analysis at the individual case level is costly and time-consuming. Therefore, any real solution must automatically summarize many examples to reason about rare, yet consequential, events that occur in surgery.

As used herein, a "biometric parameter" is a measured parameter that is indicative of the health of a patient.

As used herein, a "surgical phase" or "surgical phase" is a period of time within a surgical procedure in which an action or set of related actions is taken by the surgeon. In general, surgical phases are sequential, although it will be appreciated that the order of some the surgical phases can vary for a given procedure and that some phases can be interrupted by another phase, such that they appear more than once in a given sequence.

A "concept" in a surgical procedure is a discrete step or objective in a surgical procedure, a clinical variable, such as the Parkland Grading Scale, or a characteristic of anatomy or physiology relevant to the procedure. Examples include surgical safety notions, such as the critical view of safety in laparoscopic surgery, biometric parameters, such as blood pressure, heart rate, and blood oxygenation, a current surgical phase, the visibility of various anatomies associated with the procedure, and the physical condition of various anatomies associated with the procedure. Concepts can include visible objects, or latent, higher-level notions deduced from the surgery.

A "parameter representing a state associated with a surgical procedure" is a categorical, ordinal, or continuous parameter representing the state of a concept associated with the surgery. For example, the statistical parameter can be a categorical parameter representing exposure of anatomy to the view of the surgeon, the achievement of a critical view of safety or other surgical safety notion, a value for a biometric parameter, or similar value relevant to the concept. The state associated with each concept can be expressed as a set of emitted outputs about each concept—for example, the visibility of a region in a specific frame, or the understanding that a particular temporal phase/operative step of the surgery is taking place at that time.

A "graph" is a structure amounting to a set of objects, represented by nodes, in which some sets of the objects are directly related, represented by connection of the related nodes with an edge or hyperedge. A graph can be undirected, in which all connections are reciprocal, or directed, in which one or more connections are unidirectional.

A "location" on a graph represents the relative connectivity of a node or edge relative to the other nodes and edges. In particularly, the location can represent a degree of connectivity. In one example, a node may be included in an aggregation operation associated with another node if it is connected to the other node via a single edge or hyperedge, but not if the connection requires two or more edges. It will be appreciated that the location, or degree of connection, of a first node relative to a second node in a directed graph can be different from the location of the second node relative to the first node.

A "temporal processing network module," as used herein, is a cell or set of related cells within a neural network with some form of memory, that is, the cell or set of cells is capable of accessing data associated with inputs to the network other than a current input or training samples used in an initial training of the network. Examples of such networks include long short term memory networks, networks employing gated recurrent units, continuous time recurrent neural networks, neural Turing machines, Attention-based networks, and temporal convolutional networks.

FIG. 1 illustrates a system 100 for generating a statistical parameter representing a state of a surgical procedure from sensor data. The system 100 includes at least one sensor 102 positioned to monitor a surgical procedure on a patient. Sensors, for this purpose, can include video cameras, in the visible or infrared range, a microphone or other input device to receive comments from the surgical team at various time points within the surgery, accelerometers or radio frequency identification (RFID) devices disposed on a surgeon or an instrument associated with the surgical procedure, intraoperative imaging technologies, such as optical coherence tomography, computed tomography, X-ray imaging, sensor readings from other systems utilized in the surgical procedure, such as an anesthesia system, and sensors that detect biometric parameters of the patient, such as sphygmomanometers, in vivo pressure sensors, pulse oximeters, and electrocardiographs. In one implementation, the at least one sensor 102 includes a camera that provides one or more frames of video at each of a plurality of time periods associated with the surgery.

A non-transitory computer readable medium 112 stores machine executable instructions that are executed by an associated processor 114. It will be appreciated, however, that the system 100 could instead be implemented as dedicated hardware or programmable logic, or that the non-transitory computer readable medium 112 could comprise multiple, operatively connected, non-transitory computer readable media that are each either connected locally to the processor 114 or connected via a network connection. A sensor interface 116 receives sensor data from the sensor that represents a time period of a plurality of time periods comprising the surgical procedure. At least a portion of the sensor interface 116 will be implemented as software stored on the non-transitory computer readable medium 112, but it will be appreciated that a local bus, a network connection, or similar hardware may be used in providing the sensor data from the at least one sensor 112.

A feature extractor 118 reduces the sensor data into an output vector comprising a plurality of values representing the content of the sensor data. In particular, the feature extractor 118 extracts a plurality of features, which can be categorical, discrete, and continuous parameters representing the sensor data. In one example, the parameters can include descriptive statistics, such as measures of central tendency (e.g., median, mode, arithmetic mean, or geometric mean) and measures of deviation (e.g., range, interquartile range, variance, standard deviation, etc.) of time series of various parameters represented in the sensor data. In one example, the feature extractor 118 is a convolutional neural network that receives the sensor data without significant preprocessing and reduces the sensor data to the plurality of values representing the content of the sensor data.

A plurality of temporal processing network modules (TPNMs) 122-127 are each configured to receive the extracted plurality of numerical features, and the plurality of temporal processing network modules being connected to form a graph. A temporal processing network module, as used herein, can refer to a series of temporal processing network memory cells encoding a vector quantity. A first set of the plurality of temporal processing network modules 122-125 represent a plurality of nodes of the graph, a second set of the plurality of temporal processing network modules 126 and 127 represent a plurality of hyperedges of the graph, and each of the plurality of temporal processing network modules is updated via a message passing process according to the location of the temporal processing network module within the graph to provide a graph neural network. Details on the message passing process can be found in *Concept Graph Neural Networks for Surgical Video Understanding*, by Ban, Yutong et al, February 2022 (available at https://arxiv.org/abs/2202.13402v1). The entire contents of this paper are hereby incorporated by reference.

At least some of the nodes in the graph, and the temporal processing network modules 122-124 representing the nodes, are connected to other nodes via edges 126 and 127, such that data connections exist between nodes in the first set of plurality of temporal processing network modules 122-125 and the second set of the plurality of neural networks 126 and 127 to provide a graph structure. Some of the first set of temporal processing network modules 127 represent global nodes that represent information about the current state of the surgery outside of the specific concepts represented by the connected nodes.

At each time step, a set of attributes associated with each of the second set of the plurality of temporal processing network modules 126 and 127 are updated according the previous state of the temporal processing network module, attributes of any of the first set of the plurality of temporal processing network modules 122-124 to which they are directly connected in the graph, attributes of any of the first set of the plurality of temporal processing network modules 125 representing global nodes, and the plurality of values representing the sensor data for that time period. Each of the first set of the plurality of recurrent networks representing concept nodes 122-124 is then updated according to the values of the second set of temporal processing network modules 126 and 127 to which they are connected, the previous state of the temporal processing network module, attributes of any of the first set of the plurality of temporal processing network modules 125 representing global nodes, and the plurality of values representing the sensor data for that time period. It will be appreciated that in a directed graph, the message passing process differentiates between an input node and an output node connected by at least one hyperedge of the plurality of hyperedges during updating of the plurality of temporal processing network modules.

The output of at least one of the first set of the plurality of temporal processing network modules at each step is provided to an output device that provides a statistical parameter representing a state of the surgical procedure for the time period at an output device 130. In one example, the output device is a display that displays the parameter to a user, such as the surgeon or a member of his or her team. In another example, the output device 130 comprises a network interface that provides the output representing the state of the surgical procedure for the time period to a surgical assisted decision making system or a database for storing annotated video of the surgery.

In one example, the statistical parameter representing the state of the surgical procedure for the time period represents the likelihood that a surgical safety notion, such as the critical view of safety, has been achieved during the surgical procedure. In another implementation, where the surgical procedure is a laparoscopic cholecystectomy, the statistical parameter can represent a value for the Parkland Grading Scale. Further, in one implementation, the state of each of the first set of temporal processing network modules represents a concept associated with the surgery. In the example of a laparoscopic cholecystectomy, the state of a first temporal processing network module of the first set of temporal processing network modules represents a likelihood of exposure of the cystic plate and the state of a second temporal processing network module of the first set of temporal processing network modules represents a likelihood of exposure of the cystic duct.

Figure 2:
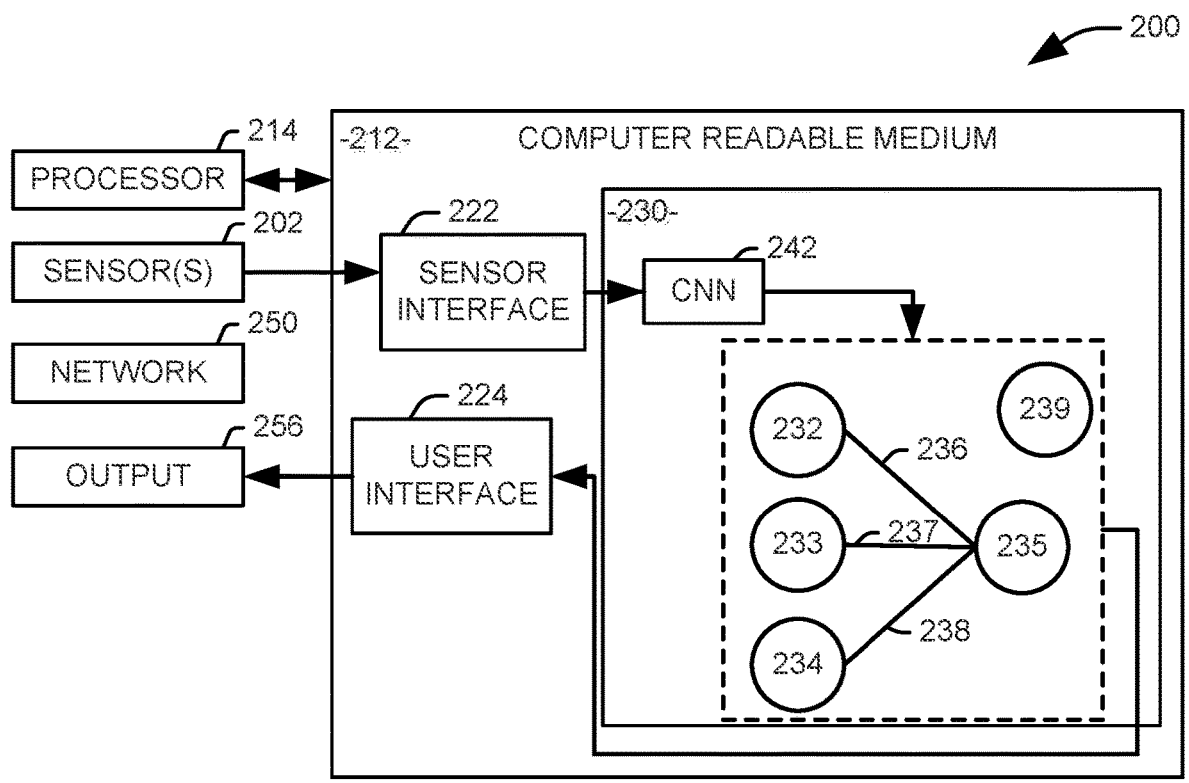
FIG. 2 illustrates another example of system for generating a statistical parameter representing a state of a surgical procedure from sensor data.

FIG. 2 illustrates one example of a system 200 for generating a statistical parameter representing a state of a surgical procedure from sensor data. While the systems and methods disclosed herein are generally applicable to any surgical procedure, the example of FIG. 2 focuses on laparoscopic cholecystectomy. Due to the highly standardized procedural steps, its stable field of view, and high performance numbers across the world, laparoscopic cholecystectomy lends itself to machine learning purposes and presents a benchmark in surgical artificial intelligence. However, in order to be applicable to a large variety of surgical procedures and reveal their true risk mitigation potential, machine learning models have to generalize and apply to various surgical notions common to multiple operations at once. Hence we propose a conceptual approach to surgical understanding and procedural actions to account for diverse aspects of surgical workflow. The conceptual surgical notions in place to relativize operational risk as well as the required reasoning about complex anatomical structures and thorough consideration of potential consequences and complications resulting from surgical actions make laparoscopic cholecystectomy an ideal target procedure for surgical AI.

An important safety measure unique to this procedure is the so called "critical view of safety" (CVS). CVS is defined as the clear dissection and visualization of the cystic duct and cystic artery, the clearing of the hepatocystic triangle of tissue, and exposure of the cystic plate. Besides that, the Parkland grading scale (PGS) provides a perspective on degree of inflammation of the gallbladder and severity of the underlying disease, upon initial inspection. The PGS involves assessment of degree of adhesions, hyperemia, distension of the gallbladder, intraabdominal fluid, liver abnormalities, and necrosis or perforation of the gallbladder. Higher PGS are associated with longer operative times, higher complication rates and elevated morbidity and mortality, making the PGS another highly clinically relevant concept to assess during laparoscopic cholecystectomy. Both of these concepts are defined and detected by a set of rules that relate to a set of observable factors. When surgeons reason about surgical procedures, they frequently utilize their conceptual understanding about how these various aspects relate to one another. Understanding surgical workflow from a minimally invasive video can be formulated as two complementary processes: (i) inferring the state of relevant surgical concepts (ii) understanding the relations between those concepts. Enabling machines to comprehend surgical workflow and assess these relevant concepts may significantly contribute to the application of machine learning and artificial intelligence in the operating room, facilitating intraoperative decision making, risk mitigation as well as holding great teaching potential for trainees.

The system 200 includes at least a camera 202 positioned to monitor a surgical procedure on a patient and provide image data as video frames. A non-transitory computer readable medium 212 stores machine executable instructions that are executed by an associated processor 214. It will be appreciated, however, that the system 200 could instead be implemented as dedicated hardware or programmable logic, or that the non-transitory computer readable medium 212 could comprise multiple, operatively connected, non-transitory computer readable media that are each either connected locally to the processor 214 or connected via a network connection.

The executable instructions stored on the non-transitory computer readable medium 212 include a sensor interface 222 that receives and conditions image data from the camera 202, a user interface 224, and a model 230. The model 230 is implemented as a graph neural network, in which a plurality of nodes 232-235, each representing a given concept, are connected by hyperedges 236-238 to form a graph. Unlike graph edges that capture binary relations, hyperedges capture more general n-nary relations, and are able to connect more than two elements, making it possible to directly model the interactions between multiple elements in the surgery, and do so efficiently. Similar to edges, hyperedges can be directed or undirected, partitioning the set of participating nodes in each edge into input and output nodes. Each node 232-234 and each hyperedge 236-238 is implemented as a long short term memory unit encoding the attribute vector associated with the node or hyperedge. Long short term memory units are a class of neural networks in which connections between nodes form a directed graph along a temporal sequence. Unlike a feedforward network, long short term memory units can incorporate feedback from states caused by earlier inputs, such that an output of the long short term memory unit for a given input can be a function of not only the input but one or more previous inputs. In a long short term memory unit, at least some hidden values from each iteration of the long short term memory unit are retained for a period of time governed by a forget gate, such that the state associated with a given time step can depend at least in part on the input from an earlier time step.

One or more global nodes 239 can be represented by other recurrent networks. The global nodes 239 accounts for the additional information about the current state of the current of the surgery, beyond the specific concepts and relations represented in the graph. In one example, the global node 239 represents the surgical procedure as a progression through a set of states, referred to herein as "surgical states" or "surgical phases." The set of surgical states can either be selected in advance, for example, by a human expert or learned as a non-parametric inference during training of the model 230. The long short term memory unit associated with the global node 239 stores a state representing the current surgical phase, that is, the surgical phase associated with the specific time, i. In one implementation, the state of the long short term memory unit is a vector of values, each representing a likelihood that one of the set of surgical states is the current surgical state. For example, the long short term memory unit associated with the global node 239 can represent a current stage of the surgery, Inputs to the recurrent networks representing each node 232-235 and 239 and hyperedge 236-238 are provided, in part, by a feature extractor 242 that receives sensor data from the sensor interface 222 representing a specific time period, i. In the illustrated implementation, the sensor data for a given time period is a frame of video captured during the surgery. The feature extractor 242 reduces the sensor data into an output vector comprising a plurality of values representing the content of the sensor data. In particular, the feature extractor 242 extracts a plurality of features, which can be categorical, discrete, and continuous parameters representing the sensor data. In one example, the parameters can include descriptive statistics, such as measures of central tendency (e.g., median, mode, arithmetic mean, or geometric mean) and measures of deviation (e.g., range, interquartile range, variance, standard deviation, etc.) of time series of various parameters represented in the sensor data.

In the illustrated example, the feature extractor 242 is a convolutional neural network (CNN) that includes convolutional layers in which nodes from a previous layer of the network are only connected to a subset of the nodes in the convolutional layer. These convolutional layers can be used to extract features from sensor data, such as audio and images. In particular, the convolutional neural network can be trained on data labelled with an appropriate output class, in this case, a surgical state represented by the sensor data, to learn useful features for extraction, such that the output vector provided by convolutional neural network is a reduced dimensionality representation of the sensor data. In the illustrated implementation, the convolutional neural network can be applied for the image encoding and the message-passing functions, $f_e$ and $f_v$, described below. A straightforward approach is to use convolutional and early fully-connected layers of a classification network, which is then concatenated along with the global vector and the aggregated neighbor nodes, to provide input to the each long short term memory unit representing a concept. During training of the model, a random dropout of the image feature/aggregated neighbor vector is applied, which forces the network to learn from the individual modal of the information, either from the images feature or the neighbor information.

As new image data is received, the various nodes 232-239 forming the graph can be updated at each time period via a message passing process in which each time frame is characterized by an edge update step and an edge-to-node aggregation step conditioned on the image data. In the edge update, for each hyperedge, k, an aggregation of the attributes associated with the nodes can be determined, such that:

$$\bar{v}_k^t = \Sigma^{v \to e}(V_k^t); v_k^t = \{v_i^t\}_{i \; s.t \; k \in N_i} \qquad \text{Eq. 1}$$

Where N represents a number of concepts represented by the graph, $v_n^t$ is a vector of attributes representing a given node, n, at a time period, t, V is the set of all nodes, and $\rho^{v \to e}$ is a graph aggregation operator that aggregates the attributes of multiple nodes based upon node inclusion in the hyperedges.

The attribute vectors representing the hyperedges can then be updated such that:

$$e_k^{t+1/2} + \phi^E(e_k^t, \bar{v}_k^t, u^t, I^t) \qquad \text{Eq. 2}$$

Where $e_k^t$ is the vector representing the $k^{th}$ edge at a time period t, $u^t$ is a vector representing the one or more global nodes 139, $I^t$ is the input image at time period t, and $\phi^E$ is a node-to-edge update operation.

Once all of the hyperedges have been updated, an edge-to-node aggregation step is performed, such that:

$$\bar{e}_k^{t+\frac{1}{2}} = \rho^{e \to v}\left(E_k^{t+\frac{1}{2}}\right); E_k^{t+\frac{1}{2}} = \left\{e_k^{t+\frac{1}{2}}\right\}_{k \in N_i} \qquad \text{Eq. 3}$$

Where E is the set of all nodes, and $\rho^{e \to v}$ is a graph aggregation operator that aggregates the attributes of multiple hyperedges based upon node inclusion in the hyperedges.

The attribute vectors representing the nodes can then be updated such that:

$$v_k^{t+1} = \phi^E\left(\bar{e}_k^{t+\frac{1}{2}}, v_i^t, u^t, I^t\right) \qquad \text{Eq. 4}$$

In the illustrated implementation, each concept node 232-235 and each hyperedge 236-238 is represented by a long short term memory (LSTM) memory unit that encodes their current state. The temporal module fuses incoming messages in addition to the current image encoder, such that:

$$\phi^E(e_k^t, \bar{v}_k^t, u^t, I^t) = LSTM\left[h_e^{k,t}, f_e(h_e^{k,t}, e_k^t, \bar{v}_k^t, u^t, I^t)\right] \qquad \text{Eq. 5}$$

$$\phi^V\left(\bar{e}_k^{t+\frac{1}{2}}, v_i^t, u^t, I^t\right) = LSTM\left[h_v^{i,t}, f_v\left(h_v^{i,t}, \bar{e}_k^{t+\frac{1}{2}}, v_i^t, u^t, I^t\right)\right] \qquad \text{Eq. 6}$$

Where h represents a hidden state of the LSTM memory unit and $f_e$ and $f_v$ are encoders of both the other neighboring nodes and hyperedges.

The model 230 can incorporate both directed and undirected hypergraphs. Directed edges allow for a chain of reasoning or causal assumptions to be implied to represent thought processes and neural inference. Our model entails several ways to represent the input/output directionality of nodes in relations. In an undirected encoding model, node updates and edge updates are performed with each single network, regardless of directionality of the node within the relation. In a directed encoding model, node and edge updates differ based on whether the node is an input node or an output node in the relation. In an individual node encoding model, for every node at every edge there is a different node update and edge update network. In practice, the design of the graph depends on each specific task and the relationships between the concepts represented by the nodes.

In one example, the model 230 targets is the critical view of safety (CVS) in laparoscopic cholecystectomy. The CVS is defined as the clear dissection of several anatomic landmarks: the cystic duct, the cystic artery, the cystic plate and hepatocystic triangle. It is a systematic safety measure designed to prevent misidentification of anatomic structures and subsequent accidental injury of the common bile duct and associated injury of the hepatic artery. Common bile duct injury presents a major complication of laparoscopic cholecystectomy and is associated with an immense increase of morbidity and mortality rates. Full achievement of CVS can be challenging especially with increasing severity of gallbladder pathology leading to major adhesions and fragility of tissue. Specifically in cases, where CVS is hard to achieve, automated recognition would augment surgical safety and provide additional supervisory clues to the surgeon. Within this concept model, the individual components of CVS are modeled as nodes and the overall achievement of CVS is defined as a relation. In particular, concept nodes, and accompanying long short term memory units, are provided for CVS, exposure of the cystic artery, exposure of the cystic duct, dissection and exposure of two and only two ductal structures leading to the gallbladder, exposure of the cystic plate, and visibility of the liver between the two ductal structures. Each of these concepts can be labelled in each frame of video used to train the model 230.

The Parkland grading scale (PGS) provides information about the degree of gallbladder inflammation upon initial laparoscopic inspection in cholecystectomy. A strong correlation has been established between higher PGS with longer operative duration, higher conversion rates to open surgery, and more frequent complications, such as bleeding, postoperative bile leakage and readmission. Among other intraoperative grading scales, it assesses gallbladder inflammation into five categories, with 5 being the worst and 1 being the least inflamed. Factors influencing the PGS score include the degree of adhesion, distention or shriveling, hyperemia, necrosis, and intra-haptic status. In our model, the factors of the Parkland scale are represented as nodes and the Parkland scale is a relation which connects the nodes, with the individual categories being represented as hyperedges. Accordingly, during training, each frame of video is labeled with a class labels representing a PGS (1, 2, 3, 4, or 5), a location of adhesions (none, majority, body, neck, buried), a degree of distention (distended, normal, shriveled), Hyperemia (yes, no), Intra-hepatic status (yes, no), and necrosis (yes, no).

It will be appreciated that the network is not limited to the disclosed examples of emissions and concepts. Emissions may include various possible surgical annotations, such as the existence of concepts with different temporal predicates ("Can the liverbed be seen in the image?", "Is there bleeding?"), spatial information about concepts ("What is the position of a cystic duct within the image?"), and additional information about concepts ("What is the six degree-of-freedom pose of a clipping tool?"). The examples herein focus on temporal annotations, indicating the presence of a particular of a concept in the image, which illustrated that certain components of the concept have been accomplished. The emission network for each concept is one fully connected layer, which projects the concept LSTM hidden state to the emission probabilities.

The determined surgical phase can be provided to a network interface 250 that communicates the determined statistical parameter to a surgical decision support system (not shown). One example of a surgical decision support system with which the system 200 can be employed can be found in U.S. Published Patent Application No. 2020/0170710, entitled "SURGICAL DECISION SUPPORT USING A DECISION THEORETIC, MODEL," the entire contents of which are hereby incorporated by reference. In one implementation, the values for the statistical parameter can be associated with corresponding resources, and the network interface 250 can notify appropriate personnel in advance that various resources are expected to be required or desired. For example, if the model 230 determines that a Parkland Grading Score is higher than expected or that a critical view of safety has not been achieved, the network interface 250 could transmit a message to a member of the operating team or another individual at the facility in which the surgical procedure is performed to request additional assistance or to schedule additional time in the operating room. Accordingly, the system 200 can be used to more efficiently allocate resources across a surgical facility.

Additionally or alternatively, the statistical parameter can be provided to a human being via an appropriate user interface 224 and output device 256, such as a video monitor, speaker, or network interface. It will be appreciated that the statistical parameter and other values representing concepts associated with the surgery and any predictions derived therefrom by the surgical assisted decision making system, can be provided directly to the surgeon to guide surgical decision making. For example, if a complication or other negative outcome is anticipated without additional radiological imaging, the surgeon could be advised to wait until the appropriate imaging can be obtained. Thus, the system 200 can be employed to assist less experienced surgeons in less common surgical procedures or unusual presentations of more common surgical procedures.

Figure 3:
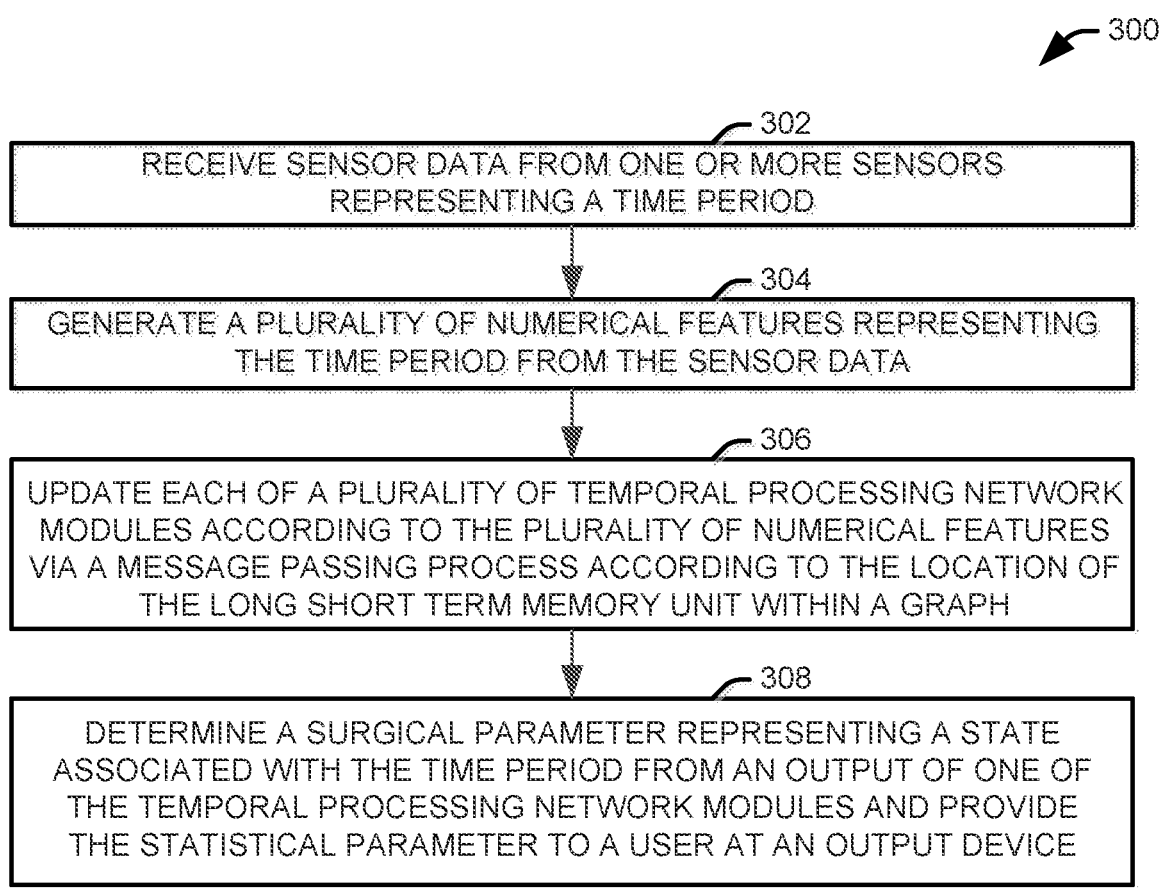
FIG. 3 illustrates a method for generating a statistical parameter representing a state of a surgical procedure from sensor data.
Figure 4:
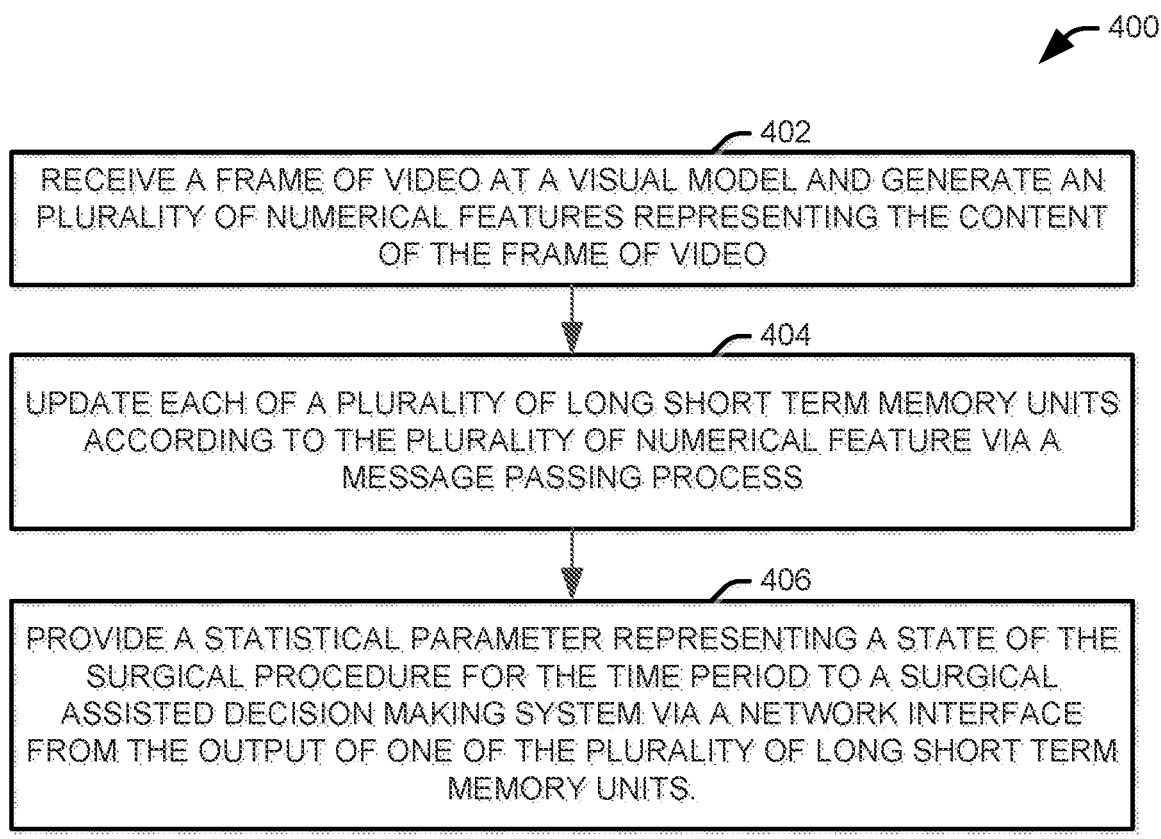
FIG. 4 illustrates another method for generating a statistical parameter representing a state of a surgical procedure from sensor data.

In view of the foregoing structural and functional features described above, methods in accordance with various aspects of the invention will be better appreciated with reference to FIGS. 3 and 4. While, for purposes of simplicity of explanation, the methods of FIGS. 3 and 4 are shown and described as executing serially, it is to be understood and appreciated that the invention is not limited by the illustrated order, as some aspects could, in accordance with the invention, occur in different orders and/or concurrently with other aspects from that shown and described herein. Moreover, not all illustrated features may be required to implement a method in accordance with an aspect of the invention. The example methods of FIGS. 3 and 4 can be implemented as machine-readable instructions that can be stored in a non-transitory computer readable medium, such as can be computer program product or other form of memory storage. The computer readable instructions corresponding to the methods of FIGS. 3 and 4 can also be accessed from memory and be executed by a processing resource (e.g., one or more processor cores).

FIG. 3 illustrates a method 300 for generating a statistical parameter representing a state of a surgical procedure from sensor data. It will be appreciated that the method will be implemented by an electronic system, which can include any of dedicated hardware, machine executable instructions stored on a non-transitory computer readable medium and executed by an associated processor, or a combination of these. In practice, the model used by the method will have already been trained on sensor data from a set of previously performed surgical procedures via a supervised or semi-supervised learning process. At 302, sensor data is received from one or more sensors representing a time period of a plurality of time periods comprising a surgical procedure. In one implementation, the sensor data is a frame of video captured at a camera.

At 304, a plurality of numerical features representing the time period are generated from the sensor data. In one implementation, the sensor data is provided to a convolutional neural network to provide the plurality of numerical features. At 306, each of a plurality of temporal processing network module units are updated according to the plurality of numerical features via a message passing process according to the location of the temporal processing network module unit within a graph. The plurality of temporal processing network module units are connected to form the graph, with a first set of the plurality of temporal processing network module units representing a plurality of nodes of the graph and a second set of the plurality of temporal processing network module units representing a plurality of hyperedges of the graph. In one example, the state of each of the first set of temporal processing network module units represents a concept associated with the surgery.

At 308, a surgical parameter representing a state associated with the time period is determined from an output of one of the temporal processing network module units and provided to a user at an output device. In one example, where the surgical procedure is a laparoscopic cholecystectomy, the statistical parameter represents a value for the Parkland Grading Scale. In another example, the statistical parameter represents the likelihood that a critical view of safety has been achieved during the surgical procedure. The resulting output can be displayed to a user or provided to a surgical assisted decision making system. In one example, a message can be transmitted to an individual at the facility in which the surgical procedure is performed via a network interface to request a surgical resource in response to the output.

FIG. 4 illustrates another method 400 for generating a statistical parameter representing a state of a surgical procedure from sensor data. At 402, a visual model receives the frame of video and generates a set of numerical features representing the content of the frame of video. In one example, where the sensor is a video camera, the observations are generated via a visual model, implemented as a discriminative classifier model that interprets the visual data. This interpretation can be indirect, for example, by finding objects within the scene that are associated with specific surgical states or world states, or by directly determining a surgical state or world state via the classification process. In one example, the visual model is implemented as an artificial neural network, such as a convolutional neural network, a cluster network, or recurrent neural network, that is trained on the plurality of time series of observations to identify the surgical state. Since the system is intended to learn from a limited amount of data and under small computational resource, a feature space for generating observations is selected to be concise and representative, with a balance between invariance and expressiveness.

In another implementation, the classification is performed from several visual cues in the videos, categorized broadly as local and global descriptor and motivated by the way surgeons deduce the phase of the surgery. These cues are used to define a feature space that captures the principal axes of variability and other discriminant factors that determine the surgical state, and then the discriminative classifier can be trained on a set of features comprising the defined feature space. The cues include color-oriented visual cues generated from a training image database of positive and negative images. Other descriptor categories for individual RGB/HSV channels can be utilized to increase dimensionality to discern features that depend on color in combination with some other property. Pixel values can also be used as features directly. The RGB/HSV components can augment both local descriptors (e.g., color values) and global descriptors (e.g., a color histogram). The relative position of organs and instruments is also an important visual cue. The position of keypoints generated via speeded-up robust features (SURF) process can be encoded with an 8×8 grid sampling of a Gaussian surface centered around the keypoint. The variance of the Gaussian defines the spatial "area of influence" of a keypoint.

Shape is important for detecting instruments, which can be used as visual cues for identifying the surgical state, although differing instrument preferences among surgeons can limit the value of shape-based cues. Shape can be encoded with various techniques, such as the Viola-Jones object detection framework, using image segmentation to isolate the instruments and match against artificial 3D models, and other methods. For local frame descriptors, a standard SURF descriptor can be used as a base, and for a global frame descriptor, grid-sampled histogram of ordered gradients (HOG) descriptors and discrete cosign transform (DCT) coefficients can be added. Texture is a visual cue used to distinguish vital organs, which tend to exhibit a narrow variety of color. Texture can be extracted using a co-occurrence matrix with Haralick descriptors, by a sampling of representative patches to be evaluated with a visual descriptor vector for each patch, and other methods. In one example, a Segmentation-based Fractal Texture Analysis (SFTA) texture descriptor is used.

At 404, each of a plurality of long short term memory units is updated according to the plurality of numerical features. The plurality of long short term memory units are connected to form a graph, with a first set of the plurality of long short term memory units representing a plurality of nodes of the graph and a second set of the plurality of long short term memory units representing a plurality of hyper-edges of the graph. Each of the plurality of long short term memory units are updated via a message passing process according to the location of the long short term memory unit within the graph. In the illustrated method 400, the state of each of the first set of long short term memory units represents a concept associated with the surgery.

At 406, a statistical parameter representing a state of the surgical procedure for the time period is provided to a surgical assisted decision making system via a network interface from the output of one of the plurality of long short term memory units. In one example, where the surgical procedure is a laparoscopic cholecystectomy, the statistical parameter represents a value for the Parkland Grading Scale. In another example, the statistical parameter represents the likelihood that a critical view of safety has been achieved during the surgical procedure. In one implementation, the statistical parameter is also provided to a user at an output device. Additionally or alternatively, a message can be transmitted at the network interface to an individual at the facility in which the surgical procedure is performed to request a surgical resource in response to the statistical parameter.

Figure 5:
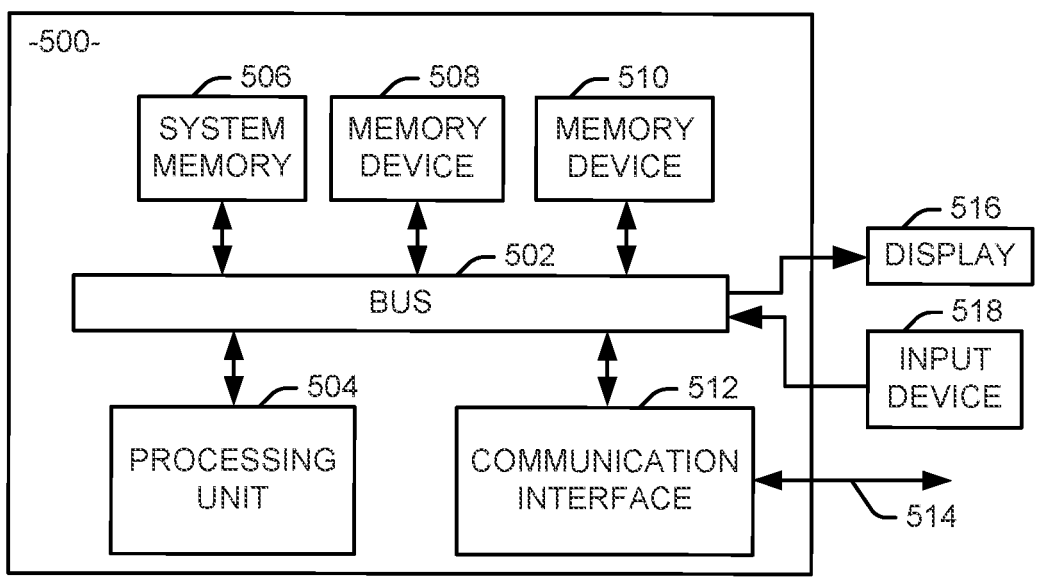
FIG. 5 illustrates a computer system that can be employed to implement systems and methods described herein.

FIG. 5 is a schematic block diagram illustrating an exemplary system 500 of hardware components capable of implementing examples of the systems and methods disclosed herein. The system 500 can include various systems and subsystems. The system 500 can be a personal computer, a laptop computer, a workstation, a computer system, an appliance, an application-specific integrated circuit (ASIC), a server, a server BladeCenter, a server farm, etc.

The system 500 can include a system bus 502, a processing unit 504, a system memory 506, memory devices 508 and 510, a communication interface 512 (e.g., a network interface), a communication link 514, a display 516 (e.g., a video screen), and an input device 518 (e.g., a keyboard, touch screen, and/or a mouse). The system bus 502 can be in communication with the processing unit 504 and the system memory 506. The additional memory devices 508 and 510, such as a hard disk drive, server, standalone database, or other non-volatile memory, can also be in communication with the system bus 502. The system bus 502 interconnects the processing unit 504, the memory devices 506-510, the communication interface 512, the display 516, and the input device 518. In some examples, the system bus 502 also interconnects an additional port (not shown), such as a universal serial bus (USB) port.

The processing unit 504 can be a computing device and can include an application-specific integrated circuit (ASIC). The processing unit 504 executes a set of instructions to implement the operations of examples disclosed herein. The processing unit can include a processing core. The additional memory devices 506, 508, and 510 can store data, programs, instructions, database queries in text or compiled form, and any other information that may be needed to operate a computer. The memories 506, 508 and 510 can be implemented as computer-readable media (integrated or removable), such as a memory card, disk drive, compact disk (CD), or server accessible over a network. In certain examples, the memories 506, 508 and 510 can comprise text, images, video, and/or audio, portions of which can be available in formats comprehensible to human beings. Additionally or alternatively, the system 500 can access an external data source or query source through the communication interface 512, which can communicate with the system bus 502 and the communication link 514.

In operation, the system 500 can be used to implement one or more parts of a system in accordance with the present invention. Computer executable logic for implementing the diagnostic system resides on one or more of the system memory 506, and the memory devices 508 and 510 in accordance with certain examples. The processing unit 504 executes one or more computer executable instructions originating from the system memory 506 and the memory devices 508 and 510. The term "computer readable medium" as used herein refers to a medium that participates in providing instructions to the processing unit 504 for execution. This medium may be distributed across multiple discrete assemblies all operatively connected to a common processor or set of related processors.

Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes but is not limited to portable or fixed storage devices, optical storage devices, wireless channels, and/or various other storage mediums capable of storing that contain or carry instruction(s) and/or data.

In the preceding description, specific details have been set forth in order to provide a thorough understanding of example implementations of the invention described in the disclosure. However, it will be apparent that various implementations may be practiced without these specific details. For example, circuits, systems, networks, processes, and other components may be shown as components in block diagram form in order not to obscure the example implementations in unnecessary detail. In other instances, well-known circuits, processes, algorithms, structures, and techniques may be shown without unnecessary detail in order to avoid obscuring the examples. The description of the example implementations will provide those skilled in the art with an enabling description for implementing an example of the invention, but it should be understood that various changes may be made in the function and arrangement of elements without departing from the spirit and scope of the invention. Accordingly, the present invention is intended to embrace all such alterations, modifications, and variations that fall within the scope of the appended claims.

What is claimed is:

1. A system comprising:
   a sensor positioned to monitor a surgical procedure on a patient such that the sensor senses objects within a scene that are associated with specific surgical states or world states to generate sensor data;
   a processor; and
   a non-transitory computer readable medium stores machine executable instructions for providing a statistical parameter representing a state of the surgical procedure for the time period, the machine executable instructions being executed by the processor to provide:
   a sensor interface that receives the sensor data from the sensor, the sensor data representing a time period of a plurality of time periods comprising the surgical procedure;

a feature extractor that generates a plurality of numerical features representing the time period from the sensor data; and a plurality of temporal processing network modules, each configured to receive the extracted plurality of numerical features, and the plurality of temporal processing network modules being connected to form a graph, with a first set of the plurality of temporal processing network modules representing a plurality of nodes of the graph, a second set of the plurality of temporal processing network modules representing a plurality of hyperedges of the graph, and each of the plurality of temporal processing network modules being updated via a message passing process according to the location of the temporal processing network module within the graph, wherein the graph is a directed graph, such that the message passing process differentiates between an input node and an output node connected by at least one hyperedge of the plurality of hyperedges during updating of the plurality of temporal processing network modules; and an output device that provides a statistical parameter representing a state of the surgical procedure for the time period to a user, the statistical parameter representing the state of the surgical procedure for the time period being derived from an output of one of the plurality of temporal processing network modules.

2. The system of claim 1, wherein the at least one sensor comprises a camera that captures frame of video.

3. The system of claim 1, wherein the feature extractor comprises a convolutional neural network.

4. The system of claim 1, further comprising a network interface that provides the output representing the state of the surgical procedure for the time period to a surgical assisted decision making system.

5. The system of claim 1, wherein the statistical parameter representing the state of the surgical procedure for the time period represents a likelihood that a critical view of safety has been achieved during the surgical procedure.

6. The system of claim 1, wherein the surgical procedure is a laparoscopic cholecystectomy, and the statistical parameter representing the state of the surgical procedure for the time period represents a value for the Parkland Grading Scale.

7. The system of claim 1, wherein the state of each of the first set of temporal processing network modules represents a concept associated with the surgery.

8. The system of claim 7, wherein the surgical procedure is a laparoscopic cholecystectomy, and a state of a first temporal processing network module of the first set of temporal processing network modules represents a likelihood of exposure of the cystic plate and a state of a second temporal processing network module of the first set of temporal processing network modules represents a likelihood of exposure of the cystic duct.

9. A method comprising:
receiving sensor data from a sensor positioned to monitor a surgical procedure on a patient, wherein the sensor senses objects within a scene that are associated with specific surgical states or world states to generate the sensor data, the sensor data representing a time period of a plurality of time periods comprising the surgical procedure;

generating a plurality of numerical features representing the time period from the sensor data;

updating each of a plurality of temporal processing network modules according to the plurality of numerical features, the plurality of temporal processing network modules being connected to form a graph, with a first set of the plurality of temporal processing network modules representing a plurality of nodes of the graph, a second set of the plurality of temporal processing network modules representing a plurality of hyperedges of the graph, and each of the plurality of temporal processing network modules being updated via a message passing process according to the location of the temporal processing network module within the graph, wherein the graph is a directed graph, such that the message passing process differentiates between an input node and an output node connected by at least one hyperedge of the plurality of hyperedges during updating of the plurality of temporal processing network modules; and providing a statistical parameter representing a state of the surgical procedure for the time period to a user at an output device, the statistical parameter representing the state of the surgical procedure for the time period being derived from an output of one of the plurality of temporal processing network modules.

10. The method of claim 9, wherein the surgical procedure is a laparoscopic cholecystectomy, and the statistical parameter representing the state of the surgical procedure for the time period represents a value for the Parkland Grading Scale.

11. The method of claim 9, further comprising provides the output representing the state of the surgical procedure for the time period to a surgical assisted decision making system via a network interface.

12. The method of claim 9, wherein the output of each of the first set of temporal processing network modules represents a concept associated with the surgery, such that the output of each of the first set of temporal processing network modules is interpretable by a human user to provide information about the surgical procedure.

13. The method of claim 9, wherein the statistical parameter representing the state of the surgical procedure for the time period represents a likelihood that a critical view of safety has been achieved during the surgical procedure.

14. The method of claim 9, wherein receiving sensor data from the sensor positioned to monitor the surgical procedure on a patient comprises receiving frames of video from a camera.

15. A method comprising:
receiving a frame of video from a sensor positioned to monitor a surgical procedure on a patient, wherein the sensor senses objects within a scene that are associated with specific surgical states or world states to generate the frame of video, the frame of video representing a time period of a plurality of time periods comprising the surgical procedure;

generating a plurality of numerical features representing the frame of video at a convolutional neural network;

updating each of a plurality of long short term memory units according to the plurality of numerical features, the plurality of long short term memory units being connected to form a graph, with a first set of the plurality of long short term memory units representing a plurality of nodes of the graph, a second set of the plurality of long short term memory units representing a plurality of hyperedges of the graph, and each of the plurality of long short term memory units being updated via a message passing process according to the location of the long short term memory unit within the graph, wherein the graph is a directed graph, such that the message passing process differentiates between an input node and an output node connected by at least one hyperedge of the plurality of hyperedges during updating of the plurality of temporal processing network modules; and providing a statistical parameter representing a state of the surgical procedure for the time period to a surgical assisted decision making system via a network interface, the statistical parameter representing the state of the surgical procedure for the time period being derived from an output of one of the plurality of long short term memory units;

wherein the state of each of the first set of long short term memory units represents a concept associated with the surgery.

16. The method of claim 15, further comprising providing a statistical parameter representing a state of the surgical procedure for the time period to a user at an output device.

17. The method of claim 15, further comprising transmitting, at the network interface, a message to an individual at the facility in which the surgical procedure is performed to request a surgical resource in response to the statistical parameter representing the state of the surgical procedure for the time period.

18. The method of claim 15, wherein the surgical procedure is a laparoscopic cholecystectomy, and the state of a first long short term memory unit of the first set of long short term memory units represents a likelihood of exposure of the cystic plate and the state of a second long short term memory unit of the first set of long short term memory units represents a likelihood of exposure of the cystic duct.

19. The method of claim 15, wherein the statistical parameter representing the state of the surgical procedure for the time period represents a likelihood that a critical view of safety has been achieved during the surgical procedure.

* * * * *